(12) United States Patent
Guevremont et al.

(10) Patent No.: US 7,041,969 B2
(45) Date of Patent: May 9, 2006

(54) METHOD AND APPARATUS FOR SELECTING INLETS OF A MULTIPLE INLET FAIMS

(75) Inventors: Roger Guevremont, Ottawa (CA); Govindanunny Thekkadath, Ottawa (CA); Greg Skotnicki, Ottawa (CA)

(73) Assignee: Ionalytics Corporation, Ottawa (CA)

( * ) Notice: Subject to any disclaimer, the term of this patent is extended or adjusted under 35 U.S.C. 154(b) by 0 days.

(21) Appl. No.: 11/068,764

(22) Filed: Mar. 2, 2005

(65) Prior Publication Data

US 2005/0194527 A1    Sep. 8, 2005

Related U.S. Application Data

(60) Provisional application No. 60/549,170, filed on Mar. 3, 2004.

(51) Int. Cl.
*H01J 49/04* (2006.01)

(52) U.S. Cl. .................. 250/285; 250/287; 250/288
(58) Field of Classification Search ............. None
See application file for complete search history.

(56) References Cited

U.S. PATENT DOCUMENTS

| | | | |
|---|---|---|---|
| 5,420,424 A | 5/1995 | Carnahan et al. | |
| 6,495,823 B1 | 12/2002 | Miller et al. | |
| 6,504,149 B1 | 1/2003 | Guevremont et al. | |
| 6,621,077 B1 | 9/2003 | Guevremont et al. | |
| 6,653,627 B1 | 11/2003 | Guevremont et al. | |
| 6,690,004 B1 | 2/2004 | Miller et al. | |
| 6,753,522 B1 | 6/2004 | Guevremont et al. | |
| 6,784,422 B1 | 8/2004 | Covey et al. | |
| 6,787,765 B1 | 9/2004 | Guevremont et al. | |
| 2004/0232326 A1 | 11/2004 | Guevremont et al. | |
| 2005/0029449 A1* | 2/2005 | Miller et al. ............. | 250/293 |

FOREIGN PATENT DOCUMENTS

WO    WO 03/067625 A1    8/2003

* cited by examiner

*Primary Examiner*—Nikita Wells
*Assistant Examiner*—Zia R. Hashmi
(74) *Attorney, Agent, or Firm*—Freedman & Associates

(57) ABSTRACT

An ion introduction system for selecting ions from one of two separate ionization sources of ions is provided. The system includes a plate having a hole formed therethrough, the plate for being disposed adjacent an ion introduction region of a gas phase ion analyzer such that the hole is selectively movable between a first location in which the hole is adjacent to a first ionization source of ions for supporting introduction of ions from the first ionization source of ions into the gas phase ion analyzer, and a second location in which the hole is adjacent to a second ionization source of ions for supporting introduction of ions from the second ionization source of ions into the gas phase ion analyzer. The system also includes a drive mechanism for driving the plate between a first position in which the hole is at the first location and a second position in which the hole is at the second location.

19 Claims, 14 Drawing Sheets

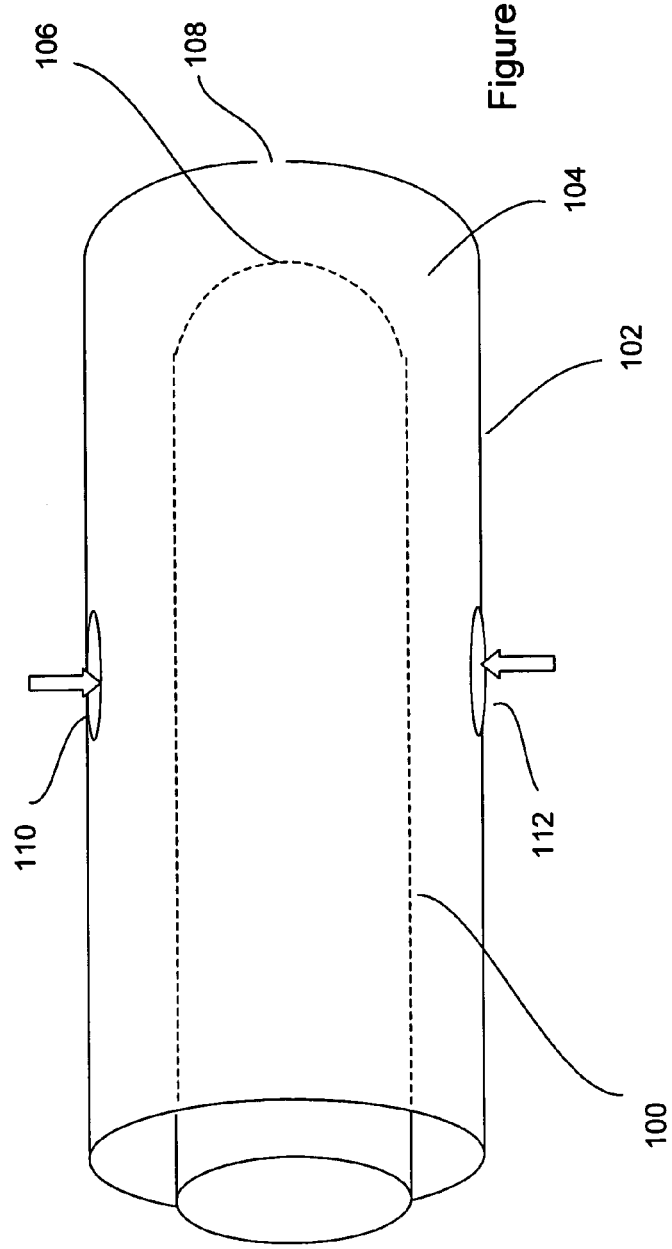
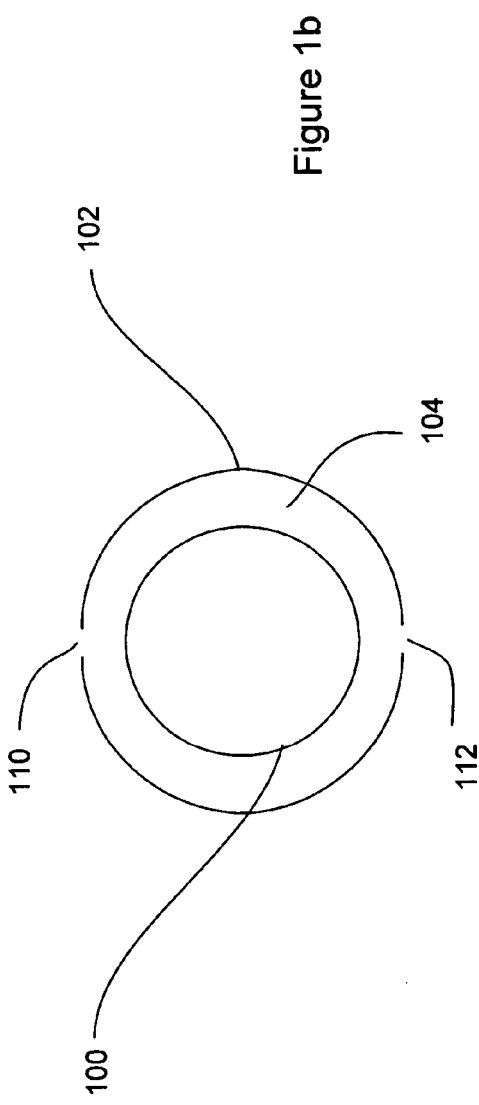

METHOD AND APPARATUS FOR SELECTING INLETS OF A MULTIPLE INLET FAIMS

This application claims benefit from U.S. Provisional application No. 60/549,170 filed on Mar. 3, 2004.

FIELD OF THE INVENTION

This invention relates generally to High-Field Asymmetric Waveform Ion Mobility Spectrometry (FAIMS) and more particularly to a selection system for multiple inlet FAIMS.

BACKGROUND OF THE INVENTION

In an analytical instrument that includes an ionization source such as for example electrospray ionization (ESI), an atmospheric pressure gas phase ion separator such as for example a high-field asymmetric waveform ion mobility spectrometer (FAIMS), and a detection system such as for example mass spectrometry (MS), it is advantageous to provide samples to the system in parallel. This allows the analytical instrument to rapidly sequence from measurements made from a first sample delivery system (HPLC for example) and from a second delivery system (preferably, but not necessarily of a type identical to the first). If the detection system is fast compared to the delivery system, then it is advantageous to multiplex a plurality of input streams to the same detector.

Multiplexing a plurality of input streams to the same detector has been attempted using a combination of ESI and MS, but such a combination is generally not very practical because the mass spectrometer is not amenable to having multiple inlets into the vacuum system. At best, the resulting gas flow into each inlet is lower than that of one opening, but more importantly the ion optics system in the vacuum system is not generally designed to accommodate ions coming from more than one ion pathway. Two or more inlets to the same MS is desirable, but is not generally practical.

Commercial systems for permitting two or more electrospray sources to operate in conjunction with one orifice into a mass spectrometer have been described. Most notable of these systems is the Micromass™ system for LockSpray™. Using the LockSpray™ system, a time-of-flight (TOF) mass spectrometer (for example) is re-calibrated intermittently during a measurement by moving a small baffle that temporarily prevents ions from an analytical source of sample from entering the MS vacuum system, whilst permitting ions from a second reference LockMass™ electrospray needle to enter the MS and be detected. Once the calibration using the reference LockMass™ compound is completed, the baffle is returned to its original position to permit the ions from the analytical ESI needle to continue to enter the MS and be measured.

If one inlet to FAIMS is used, all of the existing technology applicable to single orifice mass spectrometers would appear to be applicable. However, since FAIMS operates at atmospheric pressure, ions optionally are introduced via multiple inlets. A version of FAIMS with openings around the circumference of the outer electrode has been described previously, such as for instance in U.S. Pat. No. 6,753,522 which issued on Jun. 22, 2004 in the name of Guevremont et al., the entire contents of which are incorporated herein by reference. The ions originating from one of a plurality of ESI sources are selected by moving a ring version of the curtain plate around the FAIMS such that a single opening in the ring is situated in front of each opening in turn. However, the ring-shaped electrode is mechanically very difficult and inconvenient to actuate in an automated manner, such that the single opening is aligned precisely with a desired one of the multiple inlets into the FAIMS.

U.S. Pat. No. 6,753,522 also teaches a multiple ion inlet FAIMS system in which plural FAIMS devices are arranged around a central FAIMS device, and are controlled electronically so as to controllably provide ions to the central FAIMS device via a selected one of the multiple ion inlets. However, such an arrangement is very complicated to construct and to operate. Furthermore, the need to have multiple FAIMS devices arranged around a central FAIMS device is disadvantageous when space is limited.

It would be advantageous to provide a system and method for introducing ions into a FAIMS analyzer that overcomes at least some of the disadvantages of the prior art.

SUMMARY OF THE INVENTION

It is an object of at least some of the embodiments of the instant invention to provide an inlet selector system that supports selection between two or more inlets to FAIMS.

It is an object of at least some of the embodiments of the instant invention to provide an inlet selector system that is tolerant to alignment errors of a selector element.

According to a first aspect of the instant invention, provided is an apparatus for selecting between a first ion inlet orifice and a second ion inlet orifice of a FAIMS device, comprising: a first electrode defining a first ion inlet orifice within a first portion thereof, and defining a second ion inlet orifice within a second portion thereof; a second electrode disposed in a spaced-apart relationship with the first electrode, a space between the first electrode and the second electrode defining a FAIMS analyzer region; at least a cover for selectably covering the first ion inlet orifice and the second ion inlet orifice, the at least a cover larger than either the first ion inlet orifice or the second ion inlet orifice and providing for uncovering of a substantial area about the first ion inlet orifice and the second ion inlet orifice; and, an actuator interface for being driven by an actuator and for moving the at least a cover from a first position in which the first ion inlet orifice is uncovered by the at least a cover and the second ion inlet orifice is covered by a first portion of the at least a cover, to a second other position in which the second ion inlet orifice is uncovered by the at least a cover and the first ion inlet orifice is covered by a second portion of the at least a cover.

According to another aspect of the instant invention, provided is an apparatus for selecting between a first ion inlet orifice and a second ion inlet orifice of a FAIMS device, comprising: a first electrode defining within a first portion thereof a first ion inlet orifice having first dimensions, and defining within a second portion thereof a second ion inlet orifice having second dimensions; a second electrode disposed in a spaced-apart relationship with the first electrode, a space between the first electrode and the second electrode defining a FAIMS analyzer region; at least a cover, comprising: a first cover portion for covering the first ion inlet orifice when the at least a cover is in a first position and displaceable by an amount that is sufficient for uncovering a substantial area about the first ion inlet orifice when the cover is in a second position; a second cover portion for covering the second ion inlet orifice when the at least a cover is in the second position and displaceable by an amount that is sufficient for uncovering a substantial area about the second ion inlet orifice when the cover is in the first position;

and, an actuator interface for being driven by an actuator and for moving the at least a cover from the first position to the second position.

According to another aspect of the instant invention, provided is a method of selecting between a first ion inlet orifice and a second ion inlet orifice of a FAIMS device, comprising: providing a FAIMS device comprising a first electrode and a second electrode, the first electrode and the second electrode disposed in a spaced apart arrangement and defining a FAIMS analyzer region therebetween, the FAIMS device comprising a first ion inlet orifice defined within a first portion of the first electrode and a second ion inlet orifice defined within a second portion of the first electrode; providing a rotating actuator; and, in response to rotation of the rotating actuator in a first direction, uncovering the first ion inlet orifice and covering the second ion inlet orifice, wherein the first ion inlet orifice is covered over a first range of rotational orientations of the rotating actuator and is uncovered over a second range of rotational orientations of the rotating actuator, such that accurate rotational alignment of the rotating actuator is obviated.

BRIEF DESCRIPTION OF THE DRAWINGS

Exemplary embodiments of the invention will now be described in conjunction with the accompanying drawings, in which:

FIG. 1a shows a simplified side view of a cylindrical FAIMS device having two ion inlets formed one each through facing regions of the outer electrode;

FIG. 1b shows an end view of a cylindrical FAIMS device having two ion inlets formed one each through facing regions of the outer electrode;

FIG. 5b shows an end view of the ring-shaped cover of FIG. 5a;

DESCRIPTION OF EMBODIMENTS OF THE INSTANT INVENTION

Figure 2A:
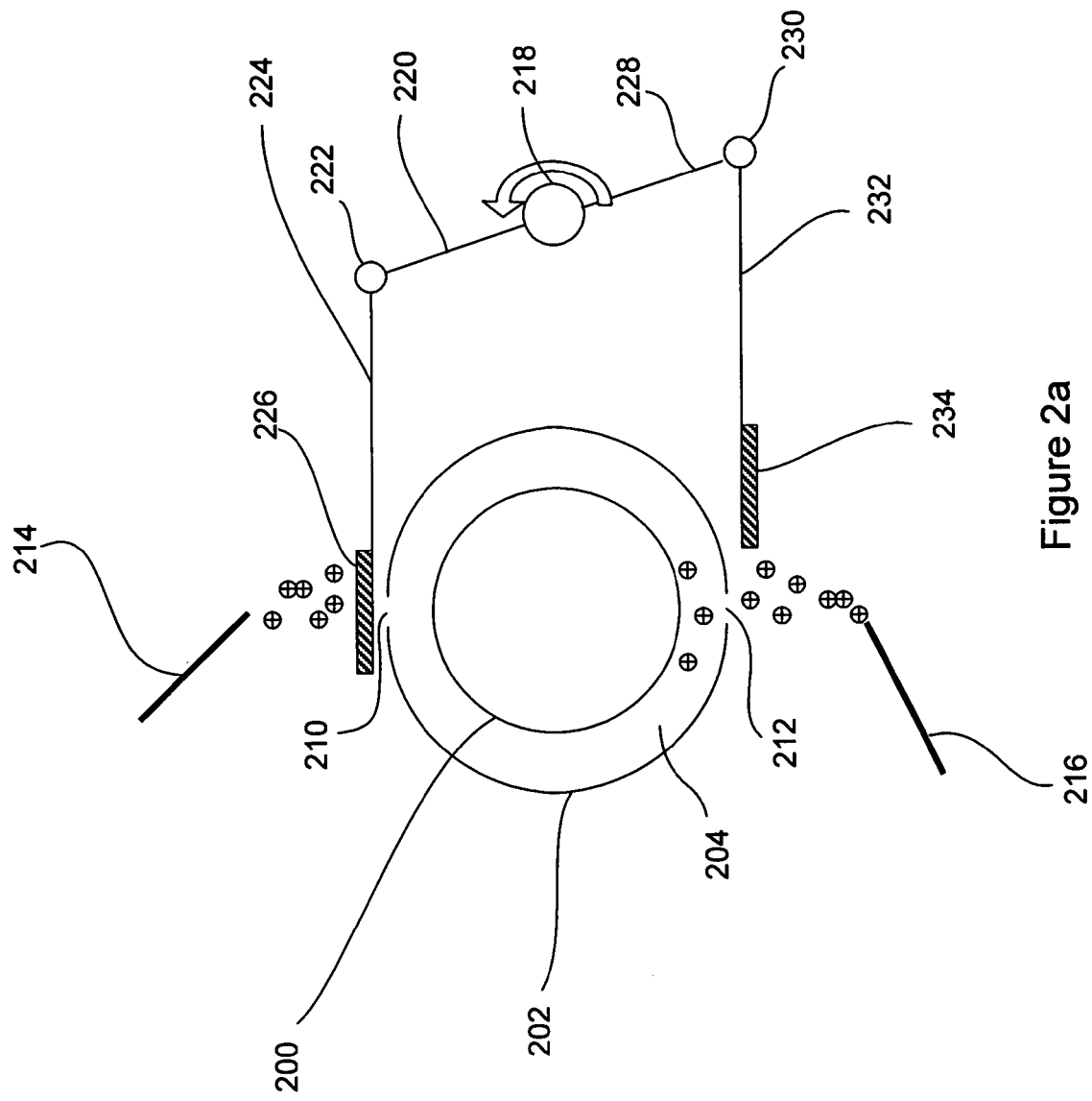
FIG. 2a shows a system according to an embodiment of the instant invention for selecting ions from two ion sources located adjacent to a FAIMS analyzer, while in a first mode of operation.

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

FIG. 1a is a simplified side view of a cylindrical FAIMS device. An inner electrode 100 is provided in an overlapping concentric arrangement with an outer electrode 102. A generally annular space between the inner electrode 100 and the outer electrode 102 defines an analyzer region 104. The inner electrode 100 includes a dome-shaped terminus 106 for directing ions out of the analyzer region 104 via an ion outlet orifice 108. In particular, the ion outlet orifice 108 is defined in the outer electrode 102 and lies along the center axis of rotation of the inner electrode 100. In the FAIMS device that is shown at FIG. 1a, two ion inlets 110 and 112 are provided within facing regions along opposite sides of the outer electrode 102. During use, a not illustrated power supply is used to provide an asymmetric waveform and a direct current compensation voltage potential between the inner electrode 100 and the outer electrode 102 so as to establish an electric field therebetween. Ions introduced into the analyzer region 104 are selectively transmitted between one of the ion inlets 110 and 112 and the ion outlet orifice 108 by the action of a carrier gas flow and/or an electric field directed along the length of the analyzer region. Those ions that posses stable trajectories under conditions of a given combination of asymmetric waveform and compensation voltage are transmitted to the ion outlet orifice 108 whereas ions that do not posses stable trajectories collide with an electrode surface and are lost. Other operational parameters of the FAIMS device, such as for instance gas temperature, gas composition, gas pressure, and the presence of temperature gradients within the gas, also affects ion separation performance. Of course, the FAIMS electrodes 100 and 102 are mounted within suitable electrically insulating material (not illustrated) and housed within an appropriate housing (not illustrated) for supporting gas flow through the device. In addition, electrical connections to the electrodes have been omitted for clarity.

FIG. 1b shows a side view of the cylindrical FAIMS device of FIG. 1a. Elements labeled with the same numerals have the same function as those illustrated in FIG. 1a. In particular, the view shown in FIG. 1b is taken along the center axis of rotation of the inner electrode 100. Ions introduced into the analyzer region 104 travel along a direction normal to the plane of the page in FIG. 1b and towards the not illustrated ion outlet orifice (which is shown as item 108 in FIG. 1a).

Referring now to FIG. 2a, shown is a system according to an embodiment of the instant invention for selecting ions from two ion sources located adjacent to a FAIMS analyzer, while in a first mode of operation. In FIG. 2a, an inner electrode 200 is provided in an overlapping concentric arrangement with an outer electrode 202, defining an analyzer region 204 therebetween. The inner electrode 200 includes a not illustrated dome-shaped terminus for directing ions out of the analyzer region 204 via a not illustrated ion outlet orifice. In particular, the ion outlet orifice is defined in the outer electrode 202 and lies along the center axis of rotation of the inner electrode 200. In the FAIMS device that is shown at FIG. 2a, two ion inlet orifices 210 and 212 are provided within facing regions along opposite sides of the outer electrode 202. During use, a not illustrated power supply is used to provide an asymmetric waveform and a direct current compensation voltage potential between the inner electrode 200 and the outer electrode 202 so as to establish an electric field therebetween. Other operational parameters of the FAIMS device, such as for instance gas temperature, gas composition, gas pressure, and the presence of temperature gradients within the gas, also affects ion separation performance. Of course, the FAIMS electrodes 200 and 202 are mounted within suitable electrically insulating material (not illustrated) and housed within an appropriate housing (not illustrated) for supporting gas flow through the device. In addition, electrical connections to the electrodes have been omitted for clarity.

Still referring to FIG. 2a, two ionization sources 214 and 216 are shown one each adjacent to the ion inlet orifices 210 and 212, respectively. In FIG. 2a, the ionization sources 214 and 216 are shown by way of non-limiting example in the form of electrospray ionization sources, but optionally any other suitable type of ionization source is used.

FIG. 2a also shows an inlet selection system according to an embodiment of the instant invention. The inlet selection system includes an actuator interface 218. The actuator interface is for being driven by a rotating actuator, such as for instance a motor of a type that is typically provided with a Waters/Micromass LockSpray™ calibration system as one non-limiting example. Of course, any other suitable rotating actuator optionally is used. In FIG. 2a, the actuator interface 218 is coupled via a first arm 220, a first rotating joint 222 and a second arm 224 to a first cover portion 226, and is coupled via a third arm 228, a second rotating joint 230 and a fourth arm 232 to a second cover portion 234. In the instant example, the first cover portion 226 is provided in the form of a first cover-plate electrode, and the second cover portion 234 is provided in the form of a second cover-plate electrode. The actuator interface 218 is for moving the first cover portion 226 from a first position in which the ion inlet orifice 210 is covered by the first cover portion 226 to a second position in which the ion inlet orifice 210 is uncovered by the first cover portion 226. Simultaneously, the actuator interface 218 is for moving the second cover portion 234 from a first position in which the ion inlet orifice 212 is uncovered by the second cover portion 234 to a second position in which the ion inlet orifice 212 is covered by the second cover portion 234. Accordingly, FIG. 2a shows the inlet selection system in a first mode of operation, in which the first cover portion 226 and the second cover portion 234 are both in the first position. In the first mode of operation, ions that are produced at the ionization source 216 are directed through the ion inlet 212 and into the analyzer region 204, whilst ions that are produced at the ionization source 214 are directed toward the first cover portion 226 where they are neutralized and the charge is carried away via the not illustrated electrical connections to the first cover portion 226.

As is shown in FIG. 2a, the first cover portion 226 is dimensioned to be larger than the ion inlet orifice 210, and the second cover portion 234 is dimensioned to be larger than the ion inlet orifice 212. Accordingly, each cover portion overlaps with a region of the outer electrode 202 about the respective ion inlet orifice, such that ions are substantially prevented from entering via a non-selected one of the ion inlet orifices. Preferably, the first through fourth arms 220, 224, 228 and 232 are stiff arms, such that rotation of the actuator interface 218 translates into simultaneous motion, but in opposite direction, of the first and second cover portions 226, 234. Of course, any other suitable mechanical linkage system for coupling the actuator interface 218 with the first cover portion 226 and with the second cover portion 234, so as to support the functionality described above, is optionally used in place of the arms and rotating joints described herein.

Figure 2B:
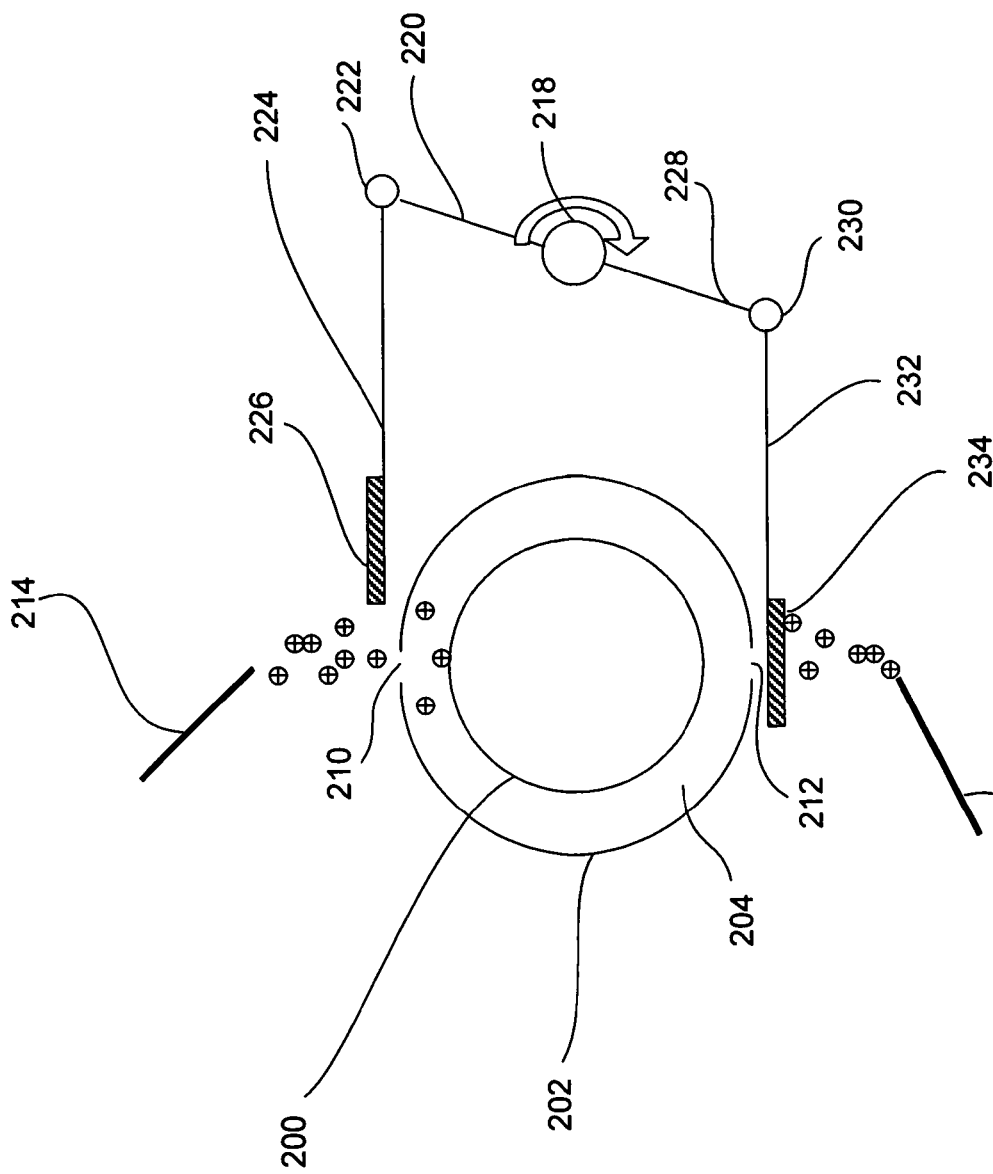
FIG. 2b shows the system of FIG. 2a in a second mode of operation.

Referring now to FIG. 2b, shown is the system of FIG. 2a while in a second mode of operation. Elements labeled with the same numerals have the same function as those illustrated in FIG. 2a. In particular, FIG. 2b shows the system of FIG. 2a subsequent to clock-wise rotation of the actuator interface 218. In FIG. 2b, the first cover portion 226 is in the second position in which the ion inlet orifice 210 is uncovered, and the second cover portion 234 is in the second position in which the ion inlet orifice 212 is covered. In the second mode of operation, ions that are produced at the ionization source 214 are directed through the ion inlet 210 and into the analyzer region 204, whilst ions that are produced at the ionization source 216 are directed toward the second cover portion 234 where they are neutralized and the charge is carried away via the not illustrated electrical connections to the second cover portion 234.

Referring now to both FIG. 2a and FIG. 2b, it is an advantage of the system according to the instant embodiment that precise rotational positioning of the actuator interface 218 is not necessary. In particular, the first cover portion 226 is moved from a first position in which the first cover portion 226 overlaps with a substantial area of the outer electrode about the ion inlet orifice 210, to a second position in which the first cover portion 226 is substantially withdrawn from the vicinity of the ion inlet orifice 210. The initial and final positions of the first cover portion are not critical, provided that the ion inlet orifice 210 is covered when the first cover portion 226 is in the first position and is uncovered when the first cover portion 226 is in the second position. There is no opening through the first cover portion that requires precise alignment with the ion inlet orifice 210 to support ion introduction therethrough, but rather the entire first cover portion 226 is simply translated out of the path between the ionization source 214 and the ion inlet orifice 210, so as to uncover the ion inlet orifice for supporting ion introduction therethrough. Accordingly, the inlet selection system according to the instant embodiment is tolerant of, or insensitive to, variations in the rotational position of the actuator interface 218 from one inlet selection cycle to another. This supports more rapid switching and more reliable switching between ion inlet orifices over time, compared to systems relying upon precise alignment of an opening with the ion inlet orifices of the FAIMS device.

Figure 2C:
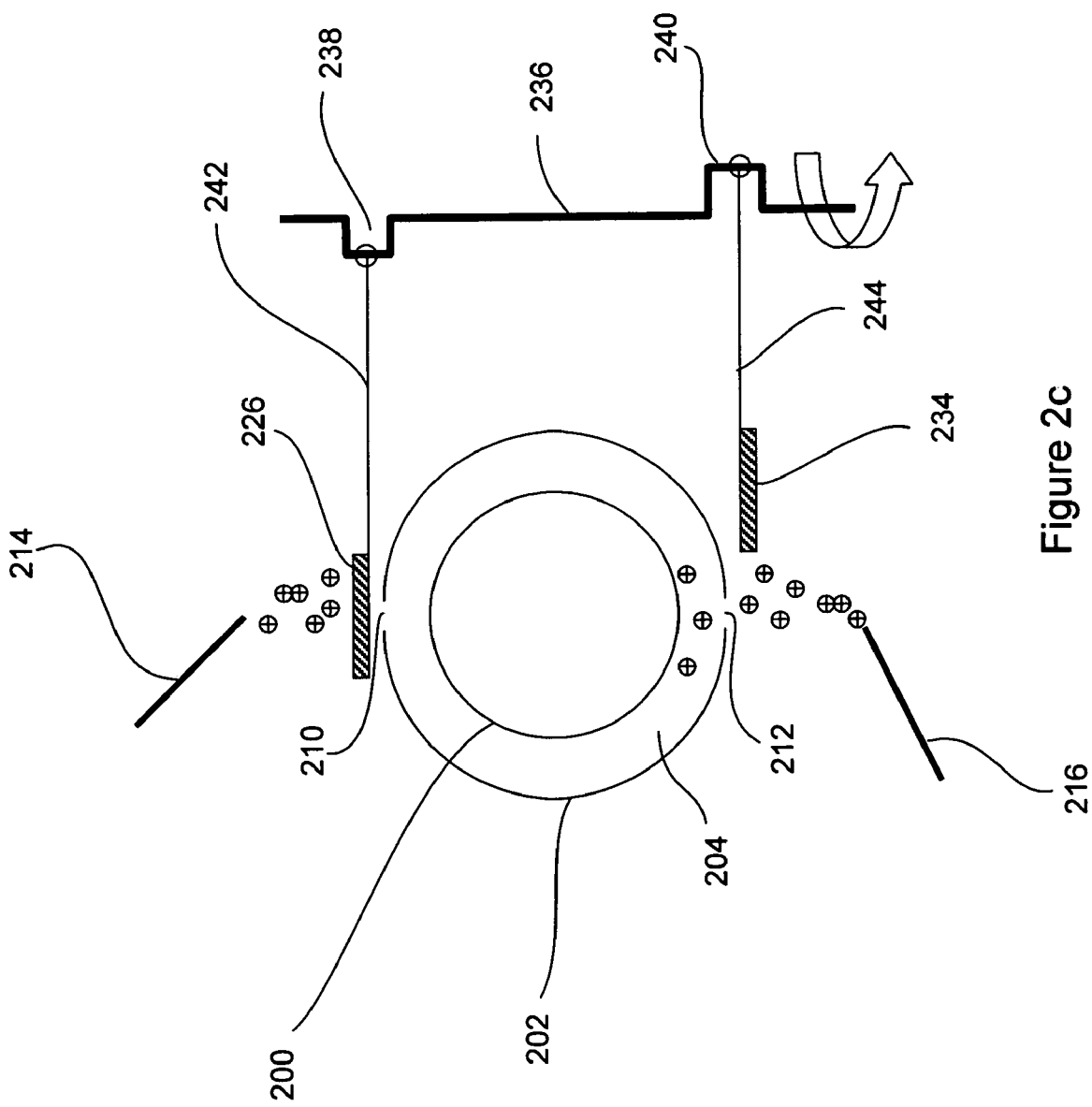
FIG. 2c shows a system according to an embodiment of the instant invention for selecting ions from two ion sources located adjacent to a FAIMS analyzer, using an alternative form of an actuator interface.
Figure 2D:
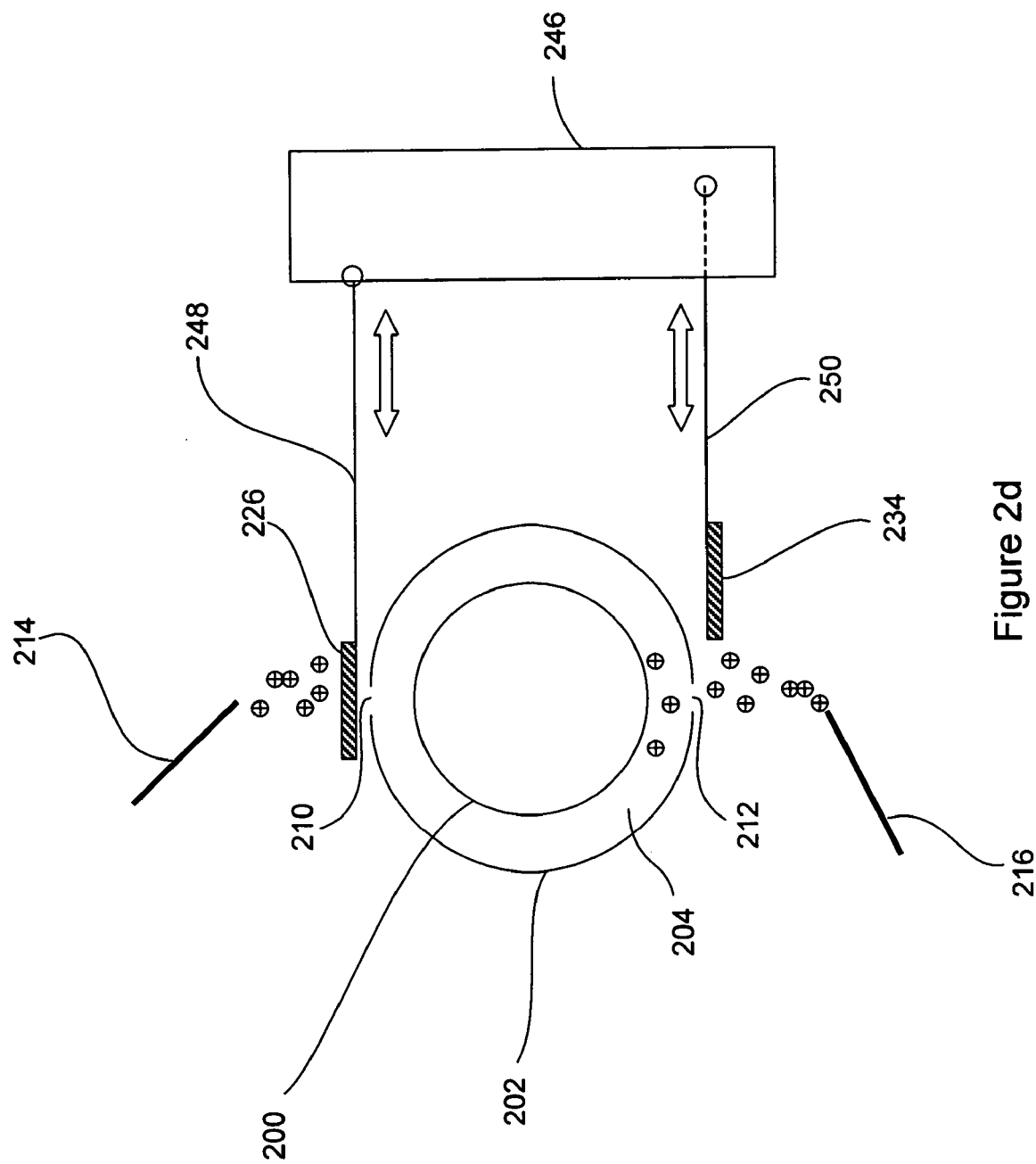
FIG. 2d shows a system according to an embodiment of the instant invention for selecting ions from two ion sources located adjacent to a FAIMS analyzer, using another alternative form of an actuator interface.

Although the various embodiments of the instant invention are described in terms of an actuator interface adapted for engaging a rotating actuator, such as for instance a rotating drive shaft of a motor, also envisaged is the use of other types of actuators, both rotating and non-rotating. Referring now to FIG. 2c, an actuator adapter in the form of a rod 236 including two eccentric cams 238 and 240 for engaging arms 242 and 244, respectively, is shown. Referring now to FIG. 2d, a non-rotating actuator 246 is shown for extending and retracting arms 248 and 250 in an alternating manner. Alternatively, other types of actuators are used with the various embodiments of the instant invention.

Figure 3A:
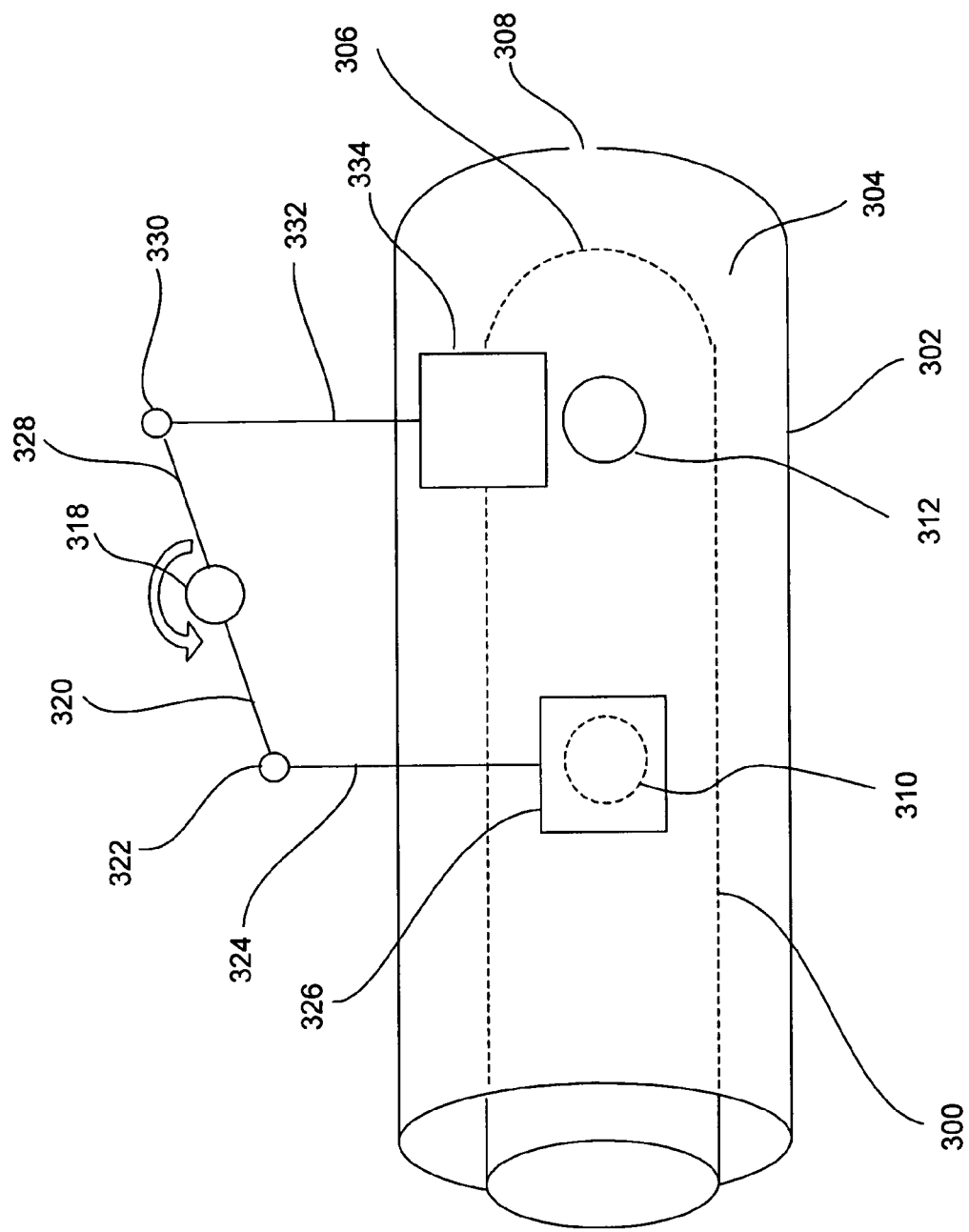
FIG. 3a shows a system according to an embodiment of the instant invention for selecting ions from two ion sources located adjacent to a FAIMS analyzer, while in a first mode of operation.

Referring now to FIG. 3a, shown is a system according to an embodiment of the instant invention for selecting ions from two ion sources located adjacent to a FAIMS analyzer, while in a first mode of operation. In FIG. 3a, an inner electrode 300 is provided in an overlapping concentric arrangement with an outer electrode 302, defining an analyzer region 304 therebetween. The inner electrode 300 includes a dome-shaped terminus 306 for directing ions out of the analyzer region 304 via an ion outlet orifice 308. In particular, the ion outlet orifice 308 is defined in the outer electrode 302 and lies along the center axis of rotation of the inner electrode 300. In the FAIMS device that is shown at FIG. 3a, two ion inlet orifices 310 and 312 are provided within adjacent regions along the length of the outer electrode 302. During use, a not illustrated power supply is used to provide an asymmetric waveform and a direct current compensation voltage potential between the inner electrode 300 and the outer electrode 302 so as to establish an electric field therebetween. Other operational parameters of the FAIMS device, such as for instance gas temperature, gas composition, gas pressure, and the presence of temperature gradients within the gas, also affects ion separation performance. Of course, the FAIMS electrodes 300 and 302 are mounted within suitable electrically insulating material (not illustrated) and housed within an appropriate housing (not illustrated) for supporting gas flow through the device. In addition, electrical connections to the electrodes have been omitted for clarity.

Still referring to FIG. 3a, two not illustrated ionization sources are provided one each adjacent to the ion inlet orifices 310 and 312. By way of non-limiting example, the ionization sources are provided in the form of electrospray ionization sources. Optionally another suitable type of ionization source is used. Further optionally, the two ionization sources include two different types of ionization sources.

FIG. 3a also shows an inlet selection system according to an embodiment of the instant invention. The inlet selection system includes an actuator interface 318. The actuator interface 318 is for being driven by a rotating actuator, such as for instance a motor of a type that is typically provided with a Waters/Micromass LockSpray™ calibration system as one non-limiting example. Of course, any other suitable rotating actuator optionally is used. In FIG. 3a, the actuator interface 318 is coupled via a first arm 320, a first rotating joint 322 and a second arm 324 to a first cover portion 326, and is coupled via a third arm 328, a second rotating joint 330 and a fourth arm 332 to a second cover portion 334. In the instant example, the first cover portion 326 is provided in the form of a first cover-plate electrode, and the second cover portion 334 is provided in the form of a second cover-plate electrode. The actuator interface 318 is for moving the first cover portion 326 from a first position in which the ion inlet orifice 310 is covered by the first cover portion 326 to a second position in which the ion inlet orifice 310 is uncovered by the first cover portion 326. Simultaneously, the actuator interface 318 is for moving the second cover portion 334 from a first position in which the ion inlet orifice 312 is uncovered by the second cover portion 334 to a second position in which the ion inlet orifice 312 is covered by the second cover portion 334. Accordingly, FIG. 3a shows the inlet selection system in a first mode of operation, in which the first cover portion 326 and the second cover portion 334 are both in the first position. In the first mode of operation, ions that are produced at an ionization source adjacent to the ion inlet 312 are directed through the ion inlet 312 and into the analyzer region 304, whilst ions that are produced at an ionization source adjacent to the ion inlet 310 are directed toward the first cover portion 326 where they are neutralized and the charge is carried away via the not illustrated electrical connections to the first cover portion 326.

As is shown in FIG. 3a, the first cover portion 326 is dimensioned to be larger than the ion inlet orifice 310, and the second cover portion 334 is dimensioned to be larger than the ion inlet orifice 312. Accordingly, each cover portion overlaps with a region of the outer electrode 302 about the respective ion inlet orifice, such that ions are substantially prevented from entering via a non-selected one of the ion inlet orifices. Preferably, the first through fourth arms 320, 324, 328 and 332 are stiff arms, such that rotation of the actuator interface 318 translates into simultaneous motion, but in opposite direction, of the first and second cover portions 326, 334. Of course, any other suitable mechanical linkage system for coupling the actuator interface 318 with the first cover portion 326 and with the second cover portion 334, so as to support the functionality described above, is optionally used in place of the arms and rotating joints described herein.

Figure 3B:
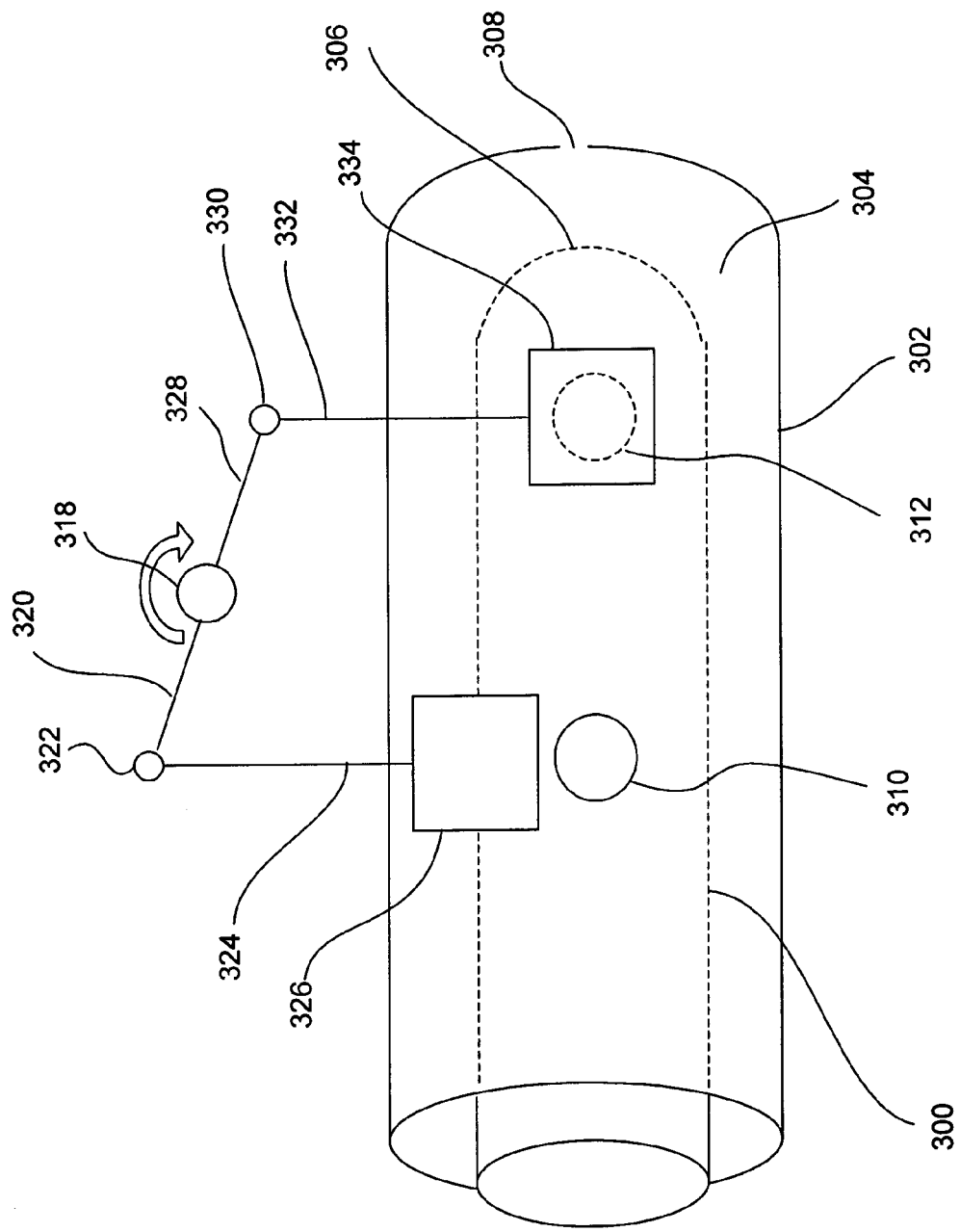
FIG. 3b shows the system of FIG. 3a in a second mode of operation.

Referring now to FIG. 3b, shown is the system of FIG. 3a while in a second mode of operation. Elements labeled with the same numerals have the same function as those illustrated in FIG. 3a. In particular, FIG. 3b shows the system of FIG. 3a subsequent to clock-wise rotation of the actuator interface 318. In FIG. 3b, the first cover portion 326 is in the second position in which the ion inlet orifice 310 is uncovered, and the second cover portion 334 is in the second position in which the ion inlet orifice 312 is covered. In the second mode of operation, ions that are produced at the ionization source adjacent to the ion inlet orifice 310 are directed through the ion inlet orifice 310 and into the analyzer region 304, whilst ions that are produced at the ionization source adjacent to the ion inlet orifice 312 are directed toward the second cover portion 334 where they are neutralized and the charge is carried away via the not illustrated electrical connections to the second cover portion 334.

Referring now to both FIG. 3a and FIG. 3b, it is an advantage of the system according to the instant embodiment that precise rotational positioning of the actuator interface 318 is not necessary. In particular, the first cover portion 326 is moved from a first position in which the first cover portion 326 overlaps with a substantial area of the outer electrode about the ion inlet orifice 310, to a second position in which the first cover portion 326 is substantially withdrawn from the vicinity of the ion inlet orifice 310. The initial and final positions of the first cover portion are not critical, provided that the ion inlet orifice 310 is covered when the first cover portion 326 is in the first position and is uncovered when the first cover portion 326 is in the second position. There is no opening through the first cover portion that requires precise alignment with the ion inlet orifice 310 to support ion introduction therethrough, but rather the entire first cover portion 326 is simply translated out of the path between the ionization source and the ion inlet orifice 310, so as to uncover the ion inlet orifice for supporting ion introduction therethrough. Accordingly, the inlet selection system according to the instant embodiment is tolerant of, or insensitive to, variations in the rotational position of the actuator interface 318 from one inlet selection cycle to another. This supports more rapid switching and more reliable switching between ion inlet orifices over time, compared to systems relying upon precise alignment of an opening with the ion inlet orifices of the FAIMS device.

Figure 4A:
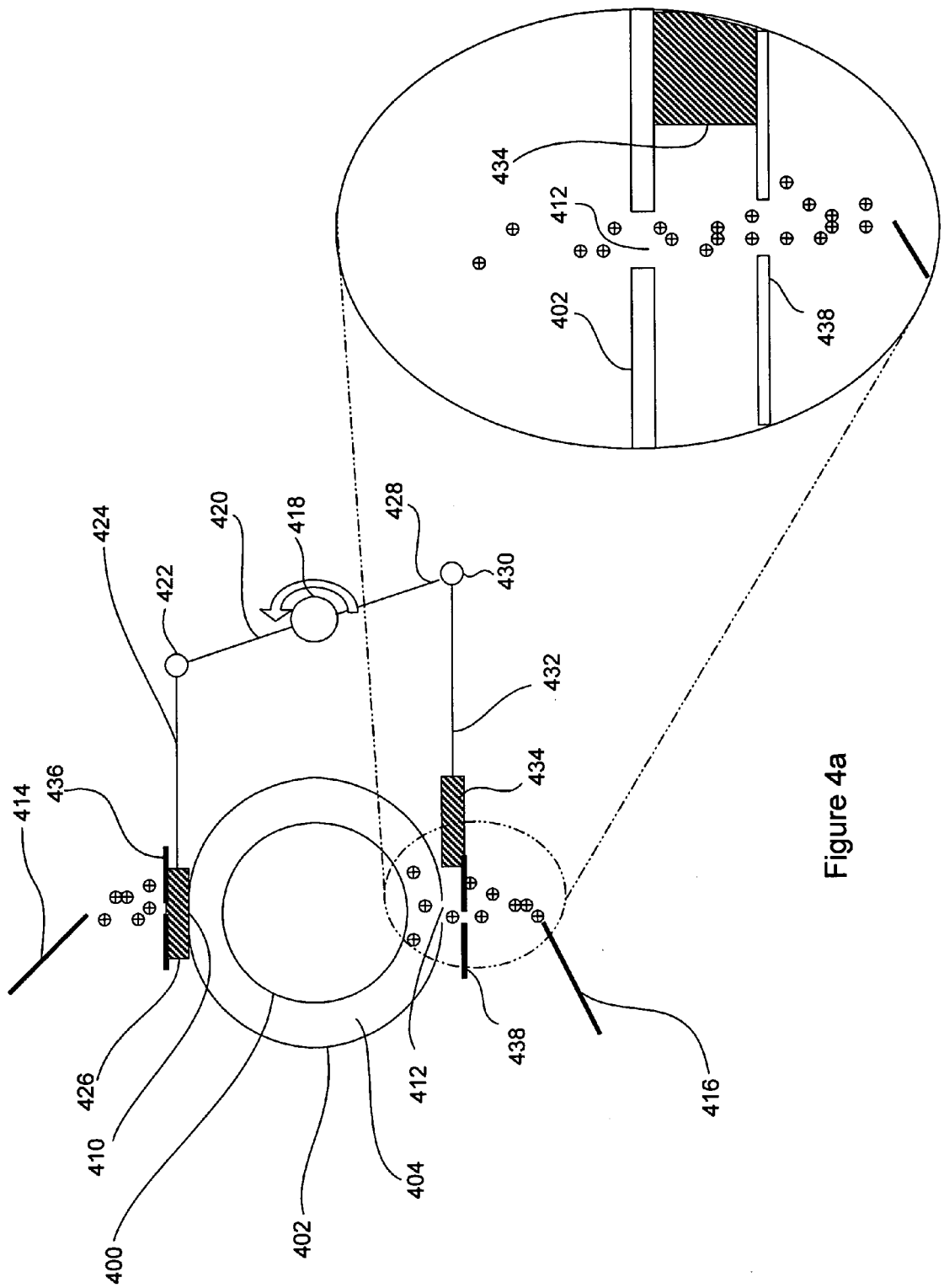
FIG. 4a shows a system according to an embodiment of the instant invention for selecting ions from two ion sources located adjacent to a FAIMS analyzer, while in a first mode of operation.

Referring now to FIG. 4a, shown is a system according to an embodiment of the instant invention for selecting ions from two ion sources located adjacent to a FAIMS analyzer, while in a first mode of operation. In FIG. 4a, an inner electrode 400 is provided in an overlapping concentric arrangement with an outer electrode 402, defining an analyzer region 404 therebetween. The inner electrode 400 includes a not illustrated dome-shaped terminus for directing ions out of the analyzer region 404 via a not illustrated ion outlet orifice. In particular, the ion outlet orifice is defined in the outer electrode 402 and lies along the center axis of rotation of the inner electrode 400. In the FAIMS device that is shown at FIG. 4a, two ion inlet orifices 410 and 412 are provided within facing regions along opposite sides of the outer electrode 402. During use, a not illustrated power supply is used to provide an asymmetric waveform and a direct current compensation voltage potential between the inner electrode 400 and the outer electrode 402 so as to establish an electric field therebetween. Other operational parameters of the FAIMS device, such as for instance gas temperature, gas composition, gas pressure, and the presence of temperature gradients within the gas, also affects ion separation performance. Of course, the FAIMS electrodes 400 and 402 are mounted within suitable electrically insulating material (not illustrated) and housed within an appropriate housing (not illustrated) for supporting gas flow through the device. In addition, electrical connections to the electrodes have been omitted for clarity.

Referring still to FIG. 4a, two ionization sources 414 and 416 are shown one each adjacent to the ion inlet orifices 410 and 412, respectively. In FIG. 4a, the ionization sources 414 and 416 are shown by way of non-limiting example in the form of electrospray ionization sources, but optionally any other suitable type of ionization source is used.

FIG. 4a also shows an inlet selection system according to an embodiment of the instant invention. The inlet selection system includes an actuator interface 418. The actuator interface is for being driven by a rotating actuator, such as for instance a motor of a type that is typically provided with a Waters/Micromass LockSpray™ calibration system as one non-limiting example. Of course, any other suitable rotating actuator optionally is used. In FIG. 4a, the actuator interface 418 is coupled via a first arm 420, a first rotating joint 422 and a second arm 424 to a first cover portion 426, and is coupled via a third arm 428, a second rotating joint 430 and a fourth arm 432 to a second cover portion 434. In this case, the first cover portion 426 is located to slide smoothly between the outer FAIMS electrode 402 and a first curtain plate electrode 436, and the second cover portion 434 is located to slide smoothly between the outer FAIMS electrode 402 and a second curtain plate electrode 438. The inset shown at FIG. 4a shows in greater detail the region around ion inlet orifice 412 when the second cover portion 434 is in the first position. In particular, the second cover portion 434 is in touching contact with the outer FAIMS electrode 402 about the ion inlet orifice 412, and is also in touching contact with the second curtain plate 438. In FIG. 4a, the second cover portion does not cover the ion inlet orifice 412. Since the cover portions are in touching contact with both the outer FAIMS electrode and with a curtain plate, it is necessary to fabricate the cover portions 426 and 434 from electrically insulating materials, to prevent a short circuit between the outer FAIMS electrode 402 and the curtain plates 436, 438 which in use are normally held at different voltages.

Referring still to FIG. 4a, the actuator interface 418 is for moving the first cover portion 426 from a first position in which the ion inlet orifice 410 is covered by the first cover portion 426 to a second position in which the ion inlet orifice 410 is uncovered by the first cover portion 426. Simultaneously, the actuator interface 418 is for moving the second cover portion 434 from a first position in which the ion inlet orifice 412 is uncovered by the second cover portion 434 to a second position in which the ion inlet orifice 412 is covered by the second cover portion 434. Accordingly, FIG. 4a shows the inlet selection system in a first mode of operation, in which the first cover portion 426 and the second cover portion 434 are both in the first position. In the first mode of operation, ions that are produced at the ionization source 416 are directed through the ion inlet orifice 412 and into the analyzer region 404, whilst ions that are produced at the ionization source 414 are directed toward the first curtain plate electrode 436 where they are neutralized and their charge is carried away via not illustrated electrical connections to the first curtain plate electrode 436.

As is shown in FIG. 4a, the first cover portion 426 is dimensioned to be larger than the ion inlet orifice 410, and the second cover portion 434 is dimensioned to be larger than the ion inlet orifice 412. Accordingly, each cover portion overlaps with a region of the outer electrode 402 about the respective ion inlet orifice, such that ions are substantially prevented from entering via a non-selected one of the ion inlet orifices. Preferably, the first through fourth arms 420, 424, 428 and 432 are stiff arms, such that rotation of the actuator interface 418 translates into simultaneous motion, but in opposite direction, of the first and second cover portions 426, 434. Of course, any other suitable mechanical linkage system for coupling the actuator interface 418 with the first cover portion 426 and with the second cover portion 434, so as to support the functionality described above, is optionally used in place of the arms and rotating joints described herein.

Figure 4B:
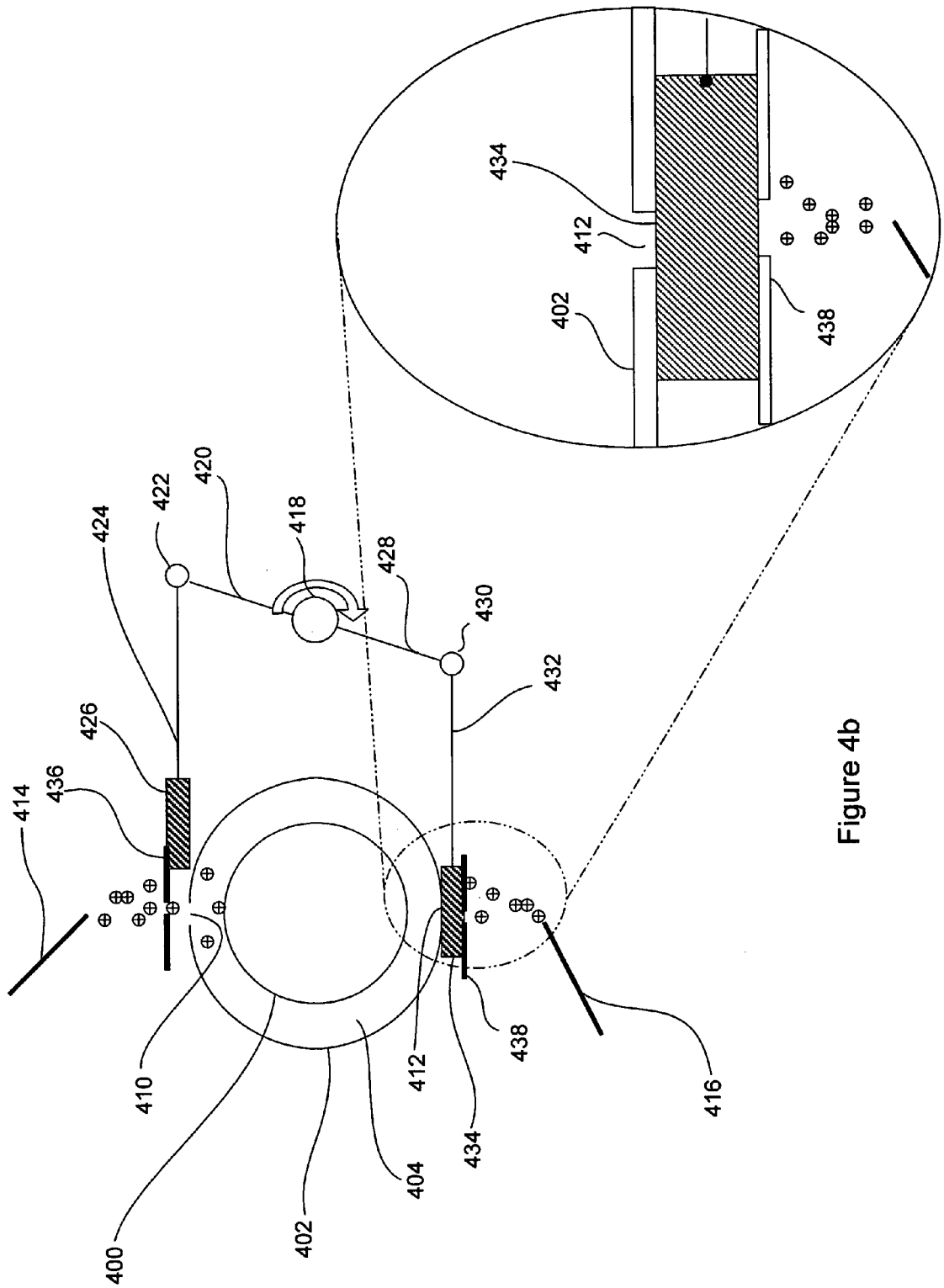
FIG. 4b shows the system of FIG. 4a in a second mode of operation.

Referring now to FIG. 4b, shown is the system of FIG. 4a while in a second mode of operation. Elements labeled with the same numerals have the same function as those illustrated in FIG. 4a. In particular, FIG. 4b shows the system of FIG. 4a subsequent to clock-wise rotation of the actuator interface 418. In FIG. 4b, the first cover portion 426 is in the second position in which the ion inlet orifice 410 is uncovered, and the second cover portion 434 is in the second position in which the ion inlet orifice 412 is covered. In the second mode of operation, ions that are produced at the ionization source 414 are directed through the ion inlet 410 and into the analyzer region 404, whilst ions that are produced at the ionization source 416 are directed toward the second curtain plate electrode 438 where they are neutralized and their charge is carried away via not illustrated electrical connections to the second curtain plate electrode 438. The inset shown at FIG. 4b shows in greater detail the region around ion inlet orifice 412 when the second cover portion 434 is in the second position. In particular, the second cover portion 434 is in touching contact with the outer FAIMS electrode 402 about the ion inlet orifice 412, and is also in touching contact with the second curtain plate 438. In FIG. 4b, the second cover portion covers the ion inlet orifice 412. Since the cover portions are in touching contact with both the outer FAIMS electrode and with a curtain plate, it is necessary to fabricate the cover portions 426 and 434 from electrically insulating materials, to prevent a short circuit between the outer FAIMS electrode 402 and the curtain plates 436, 438 which in use are normally held at different voltages.

Referring now to both FIG. 4a and FIG. 4b, it is an advantage of the system according to the instant embodiment that precise rotational positioning of the actuator interface 418 is not necessary. In particular, the first cover portion 426 is moved from a first position in which the first cover portion 426 overlaps with a substantial area of the outer electrode about the ion inlet orifice 410, to a second position in which the first cover portion 426 is substantially withdrawn from the vicinity of the ion inlet orifice 410. The initial and final positions of the first cover portion are not critical, provided that the ion inlet orifice 410 is covered when the first cover portion 426 is in the first position and is uncovered when the first cover portion 426 is in the second position. There is no opening through the first cover portion that requires precise alignment with the ion inlet orifice 410 to support ion introduction therethrough, but rather the entire first cover portion 426 is simply translated out of the path between the ionization source 414 and the ion inlet orifice 410, so as to uncover the ion inlet orifice for supporting ion introduction therethrough. Accordingly, the inlet selection system according to the instant embodiment is tolerant of, or insensitive to, variations in the rotational position of the actuator interface 418 from one inlet selection cycle to another. This supports more rapid switching and more reliable switching between ion inlet orifices over time, compared to systems relying upon precise alignment of an opening with the ion inlet orifices of the FAIMS device.

In the systems shown at FIGS. 4a and 4b, flows of gases into the two curtain plate regions defined by the space between each of first and second curtain plate electrodes 436, 438 and the outer electrode 402 are optionally provided by a single gas source. Since the rotation of the actuator interface simultaneously closes the opening in the first curtain plate electrode 436 and the first ion inlet orifice 410 while opening the orifices in the second curtain plate electrode 438 and the second ion inlet orifice 412, a single supply of gas to both regions through a simple T-junction supplies identical flows to either of the regions as they are activated. Preferably there is no time during which both are completely covered. In an alternative system for supplying gas, independent gas flows are provided to the two curtain plate regions. However, provision for operation with the opening in the curtain plate and the ion inlet into FAIMS blocked by the cover plate as shown in FIGS. 4 and 5, must be considered. In this second approach it is possible that gases of different composition could be used for each curtain plate region. In the mode of operation where the gas from the curtain plate region enters the FAIMS analyzer region through the ion inlet orifice and assists in carrying the ions to the ion outlet, it is expected that the change of composition of the carrier gas, in conjunction with the selection of a different inlet and corresponding ion source, does not occur within a time greatly different than a time necessary for the flow of ions from the newly selected source to reach the ion outlet.

Figure 5B:
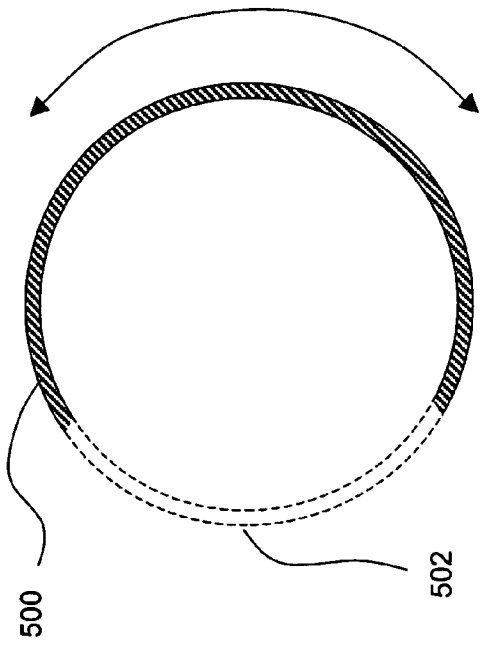
Figure 5D:
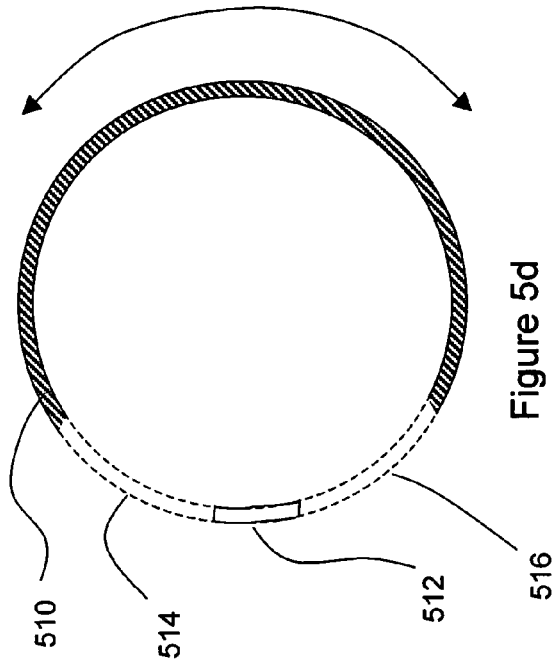
FIG. 5d shows an end view of the ring-shaped cover of FIG. 5c.
Figure 5A:
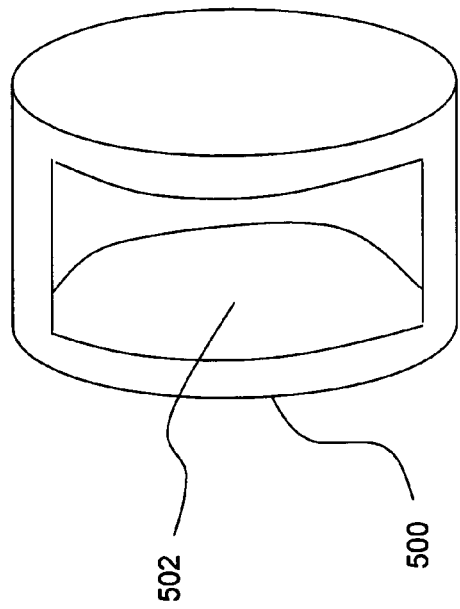
FIG. 5a shows a view of a ring-shaped cover for use with an ion inlet selector system according to an embodiment of the instant invention.

Referring now to FIG. 5a, shown is a view of a ring-shaped cover for use with an ion inlet selecting system according to an embodiment of the instant invention. The ring-shaped cover 500 includes an opening 502 defined within a portion thereof. The opening 502 is dimensioned to be larger than an ion inlet orifice that is to be selectively covered and uncovered using the ring-shaped cover 500. FIG. 5b shows a side view of the ring-shaped cover of FIG. 5a, wherein elements labeled with the same numerals have the same function as those illustrated in FIG. 5a.

Figure 5C:
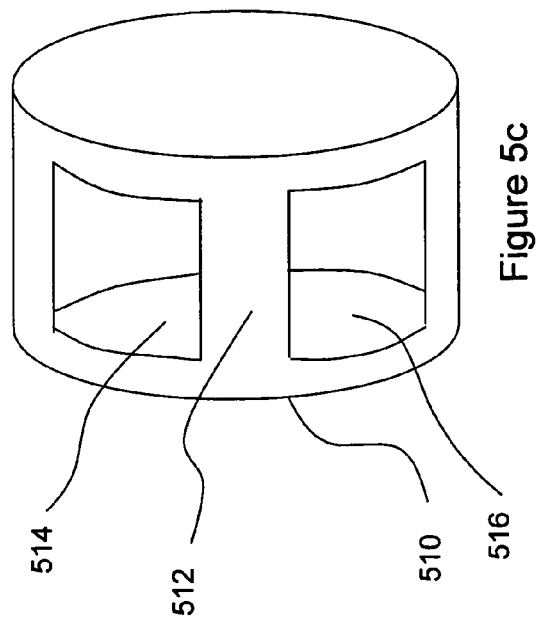
FIG. 5c shows a view of another ring-shaped cover for use with an ion inlet selector system according to an embodiment of the instant invention.

Referring now to FIG. 5c, shown is a view of another ring-shaped cover for use with an ion inlet selecting system according to an embodiment of the instant invention. The ring-shaped cover 510 includes two openings 514 and 516 defined within portions thereof, which openings are separated by a separator 512. Each opening 514 and 516 is dimensioned to be larger than an ion inlet orifice that is to be selectively covered and uncovered using the ring-shaped cover 510. FIG. 5d shows a side view of the ring-shaped cover of FIG. 5c, wherein elements labeled with the same numerals have the same function as those illustrated in FIG. 5c.

Figure 5F:
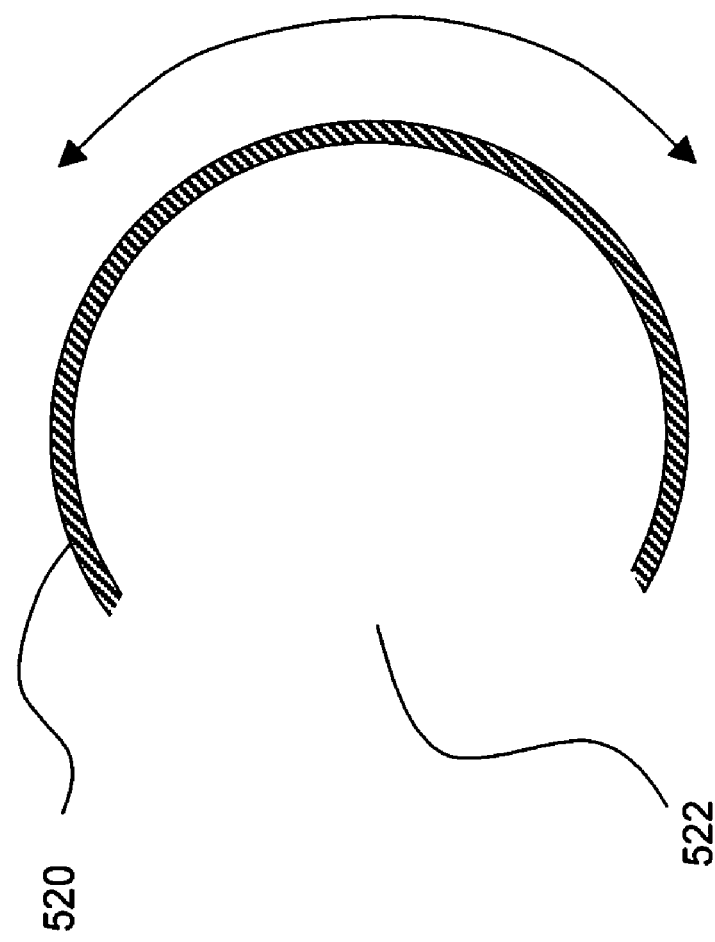
FIG. 5f shows an end view of the ring-shaped cover of FIG. 5e.
Figure 5E:
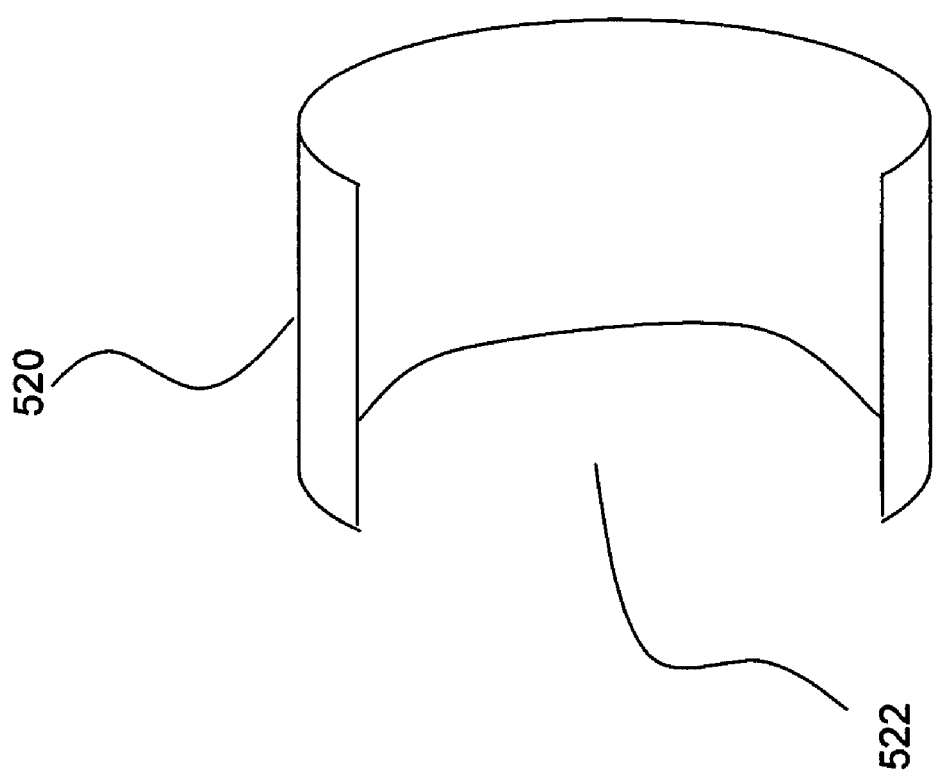
FIG. 5e shows a view of another ring-shaped cover for use with an ion inlet selector system according to an embodiment of the instant invention.

Referring now to FIG. 5e, shown is a view of another ring-shaped cover for use with an ion inlet selecting system according to an embodiment of the instant invention. The ring-shaped cover 520 is generally C-shaped when viewed end-on, as shown in FIG. 5f. A space 522, which is dimensioned to be larger than an ion inlet orifice that is to be selectively covered and uncovered using the ring-shaped cover 520, is provided.

Figure 6A:
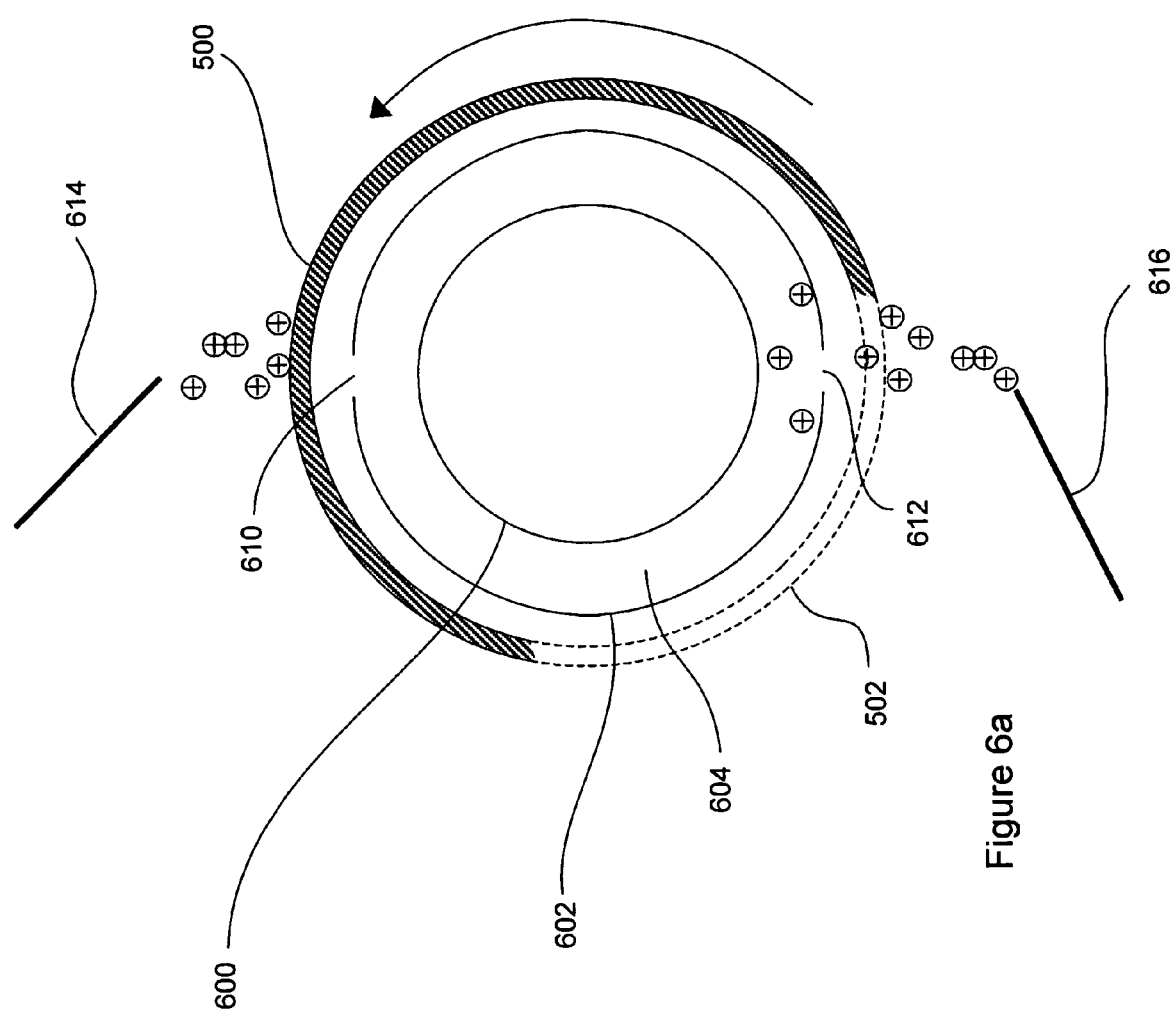
FIG. 6a shows an end view of a system according to an embodiment of the instant invention for selecting ions from two ion sources located adjacent to a FAIMS analyzer, while in a first mode of operation.

Referring now to FIG. 6a, shown is an end view of a system according to an embodiment of the instant invention for selecting ions from two ion sources located adjacent to a FAIMS analyzer, while in a first mode of operation. In FIG. 6a, an inner electrode 600 is provided in an overlapping concentric arrangement with an outer electrode 602, defining an analyzer region 604 therebetween. The inner electrode 600 includes a not illustrated dome-shaped terminus for directing ions out of the analyzer region 604 via a not illustrated ion outlet orifice. In particular, the ion outlet orifice is defined in the outer electrode 602 and lies along the center axis of rotation of the inner electrode 600. In the FAIMS device that is shown at FIG. 6a, two ion inlet orifices 610 and 612 are provided within facing regions along opposite sides of the outer electrode 602. During use, a not illustrated power supply is used to provide an asymmetric waveform and a direct current compensation voltage potential between the inner electrode 600 and the outer electrode 602 so as to establish an electric field therebetween. Other operational parameters of the FAIMS device, such as for instance gas temperature, gas composition, gas pressure, and the presence of temperature gradients within the gas, also affects ion separation performance. Of course, the FAIMS electrodes 600 and 602 are mounted within suitable electrically insulating material (not illustrated) and housed within an appropriate housing (not illustrated) for supporting gas flow through the device. In addition, electrical connections to the electrodes have been omitted for clarity.

Still referring to FIG. 6a, two ionization sources 614 and 616 are shown one each adjacent to the ion inlet orifices 610 and 612, respectively. In FIG. 6a, the ionization sources 614 and 616 are shown by way of non-limiting example in the form of electrospray ionization sources, but optionally any other suitable type of ionization source is used.

FIG. 6a also shows an inlet selection system according to an embodiment of the instant invention. The inlet selection system includes a ring-shaped cover 500 including an opening 502 defined within a portion thereof. In particular, the ring-shaped cover 500 is provided in the form of an electrically conductive ring-shaped cover electrode. The ring-shaped cover 500 is moveable between a first position in which the ion inlet orifice 610 is covered by a first portion of the ring-shaped cover 500 whilst the ion inlet orifice 616 is uncovered by the opening 502, to a second position in which the ion inlet orifice 610 is uncovered by the opening 502 whilst the ion inlet orifice 612 is covered by a second portion of the ring-shaped cover 500. The first and second portions of the ring-shaped cover 500 are optionally same portions or different portions of the ring-shaped cover 500. Accordingly, FIG. 6a shows the inlet selection system in a first mode of operation, in which the ion inlet orifice 610 is covered and the inlet orifice 612 is uncovered. In the first mode of operation, ions that are produced at the ionization source 616 are directed through the ion inlet 612 and into the analyzer region 604, whilst ions that are produced at the ionization source 614 are directed toward the outward facing surface of the ring-shaped cover 500, where they are neutralized and the charge is carried away via the not illustrated electrical connections to the ring-shaped cover 500.

As is shown in FIG. 6a, the opening 502 in the ring-shaped cover 500 is dimensioned to be larger than the ion inlet orifice 610 or 612. Accordingly, the opening 502 uncovers a selected one of the ion inlet orifice 610 or 612, as well as a substantial area of the outer electrode 602 about the selected one of the ion outlet orifice 610 or 612. In addition, the ring-shaped cover 500 is dimensioned to overlap with a region of the outer electrode 602 about the non-selected ion inlet orifice 610 or 612, such that ions are substantially prevented from entering via the non-selected ion inlet orifice.

Figure 6B:
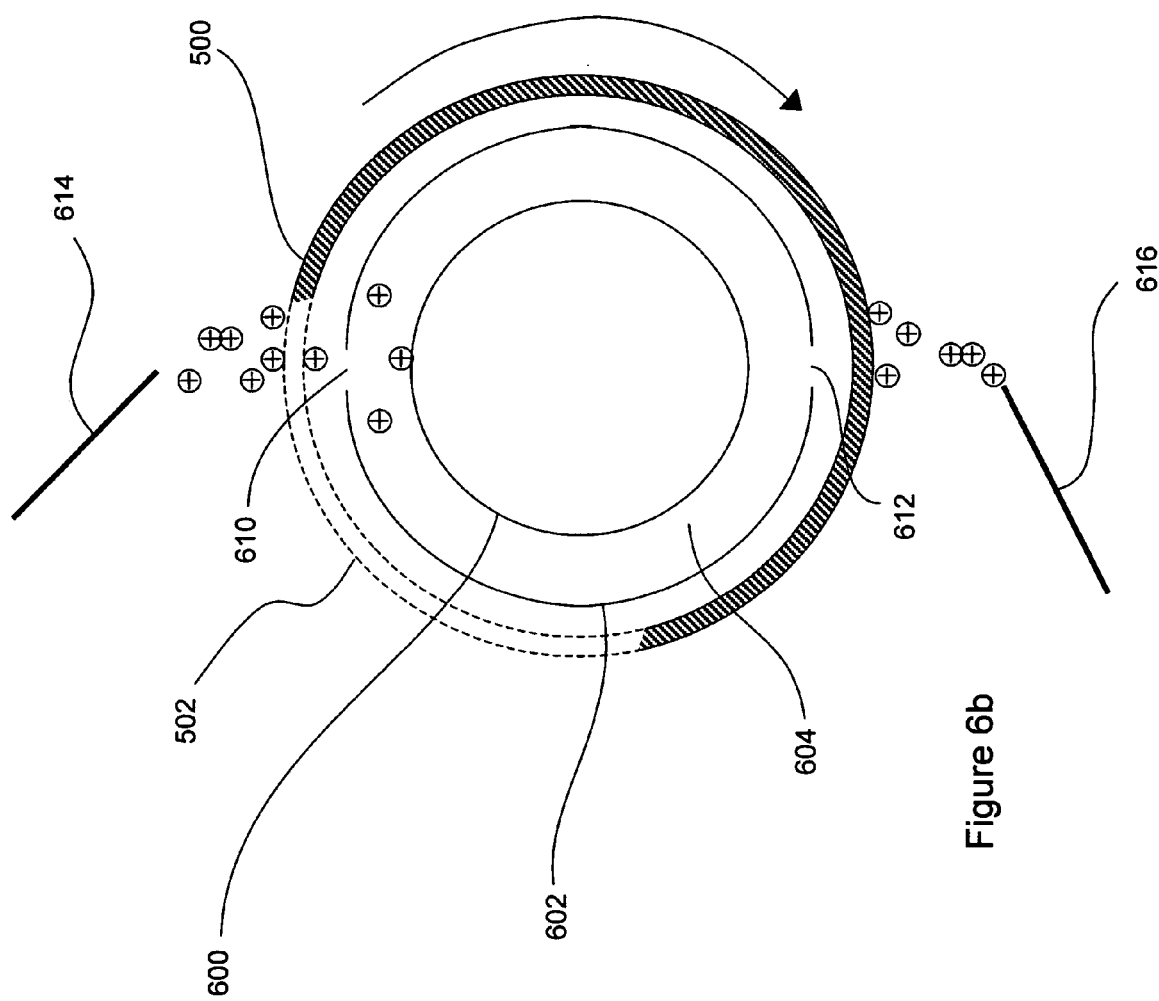
FIG. 6b shows the system of FIG. 6a in a second mode of operation.

Referring now to FIG. 6b, shown is the system of FIG. 6a while in a second mode of operation. Elements labeled with the same numerals have the same function as those illustrated in FIG. 6a. In particular, FIG. 6b shows the system of FIG. 6a subsequent to clock-wise rotation of the ring-shaped cover 500. In the second mode of operation, ions that are produced at the ionization source 614 are directed through the ion inlet 610 and into the analyzer region 604, whilst ions that are produced at the ionization source 616 are directed toward the outward facing surface of the ring-shaped cover 500, where they are neutralized and the charge is carried away via the not illustrated electrical connections to the ring-shaped cover 500.

Referring now to both FIG. 6a and FIG. 6b, it is an advantage of the system according to the instant embodiment that precise rotational positioning of the ring-shaped cover 500 is not necessary. In particular, the initial and final orientations of the ring-shaped cover 500 are not critical. There is no opening through the ring-shaped cover 500 that requires precise alignment with the ion inlet orifice 610 or 612 to support ion introduction therethrough, but rather the ring-shaped cover 500 is simply rotated until the opening 502 completely uncovers the appropriate ion inlet orifice. Accordingly, the inlet selection system according to the instant embodiment is tolerant of, or insensitive to, variations in the rotational position of the ring-shaped cover 500 from one inlet selection cycle to another. This supports more rapid switching and more reliable switching between ion inlet orifices over time, compared to systems relying upon precise alignment of an opening with the ion inlet orifices of the FAIMS device.

Figure 7:
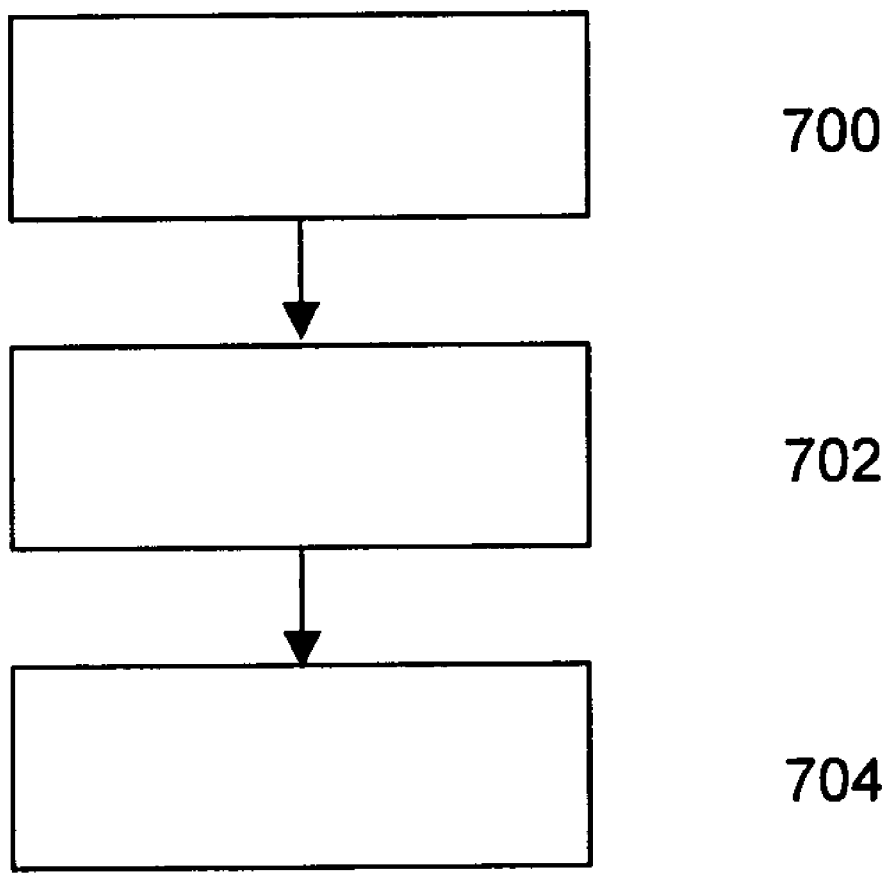
FIG. 7 shows a simplified flow diagram of a method according to an embodiment of the instant invention.

Referring now to FIG. 7, shown is a simplified flow diagram of a method according to an embodiment of the instant invention. At step 700 a FAIMS device is provided, comprising a first electrode and a second electrode, the first electrode and the second electrode disposed in a spaced apart arrangement and defining a FAIMS analyzer region therebetween. The FAIMS device comprises a first ion inlet orifice defined within a first portion of the first electrode and a second ion inlet orifice defined within a second portion of the first electrode. At step 702, a rotating actuator is provided. At step 704, in response to rotation of the rotating actuator in a first direction, the first ion inlet orifice is uncovered and the second ion inlet orifice is covered. In particular, the first ion inlet orifice is covered over a first range of rotational orientations of the rotating actuator and is uncovered over a second range of rotational orientations of the rotating actuator, such that accurate rotational alignment of the rotating actuator is obviated.

Numerous other embodiments may be envisaged without departing from the spirit and scope of the invention.

What is claimed is:

1. An apparatus for selecting between a first ion inlet orifice and a second ion inlet orifice of a FAIMS device, comprising:
    a first electrode defining a first ion inlet orifice within a first portion thereof, and defining a second ion inlet orifice within a second portion thereof;
    a second electrode disposed in a spaced-apart relationship with the first electrode, a space between the first electrode and the second electrode defining a FAIMS analyzer region;
    at least a cover for selectably covering the first ion inlet orifice and the second ion inlet orifice, the at least a cover larger than either the first ion inlet orifice or the second ion inlet orifice and providing for uncovering of a substantial area about the first ion inlet orifice and the second ion inlet orifice; and,
    an actuator interface for being driven by an actuator and for moving the at least a cover from a first position in which the first ion inlet orifice is uncovered by the at least a cover and the second ion inlet orifice is covered by a first portion of the at least a cover, to a second other position in which the second ion inlet orifice is uncovered by the at least a cover and the first ion inlet orifice is covered by a second portion of the at least a cover.

2. An apparatus according to claim 1, comprising an actuator coupled to the actuator interface, the actuator for driving the actuator interface.

3. An apparatus according to claim 2, wherein the actuator is a rotating actuator.

4. An apparatus according to claim 1, wherein the at least a cover comprises a first cover member containing the first portion of the at least a cover and a second cover member distinct from the first cover member and containing the second portion of the at least a cover.

5. An apparatus according to claim 4, wherein the first cover member and the second cover member are fabricated from an electrically insulating material.

6. An apparatus according to claim 4, wherein the first cover member and the second cover member are fabricated from an electrically conductive material.

7. An apparatus according to claim 1, comprising a coupling mechanism disposed between the actuator interface and the at least a cover, for moving simultaneously the first portion of the at least a cover and the second portion of the at least a cover.

8. An apparatus for selecting between a first ion inlet orifice and a second ion inlet orifice of a FAIMS device, comprising:

a first electrode defining within a first portion thereof a first ion inlet orifice having first dimensions, and defining within a second portion thereof a second ion inlet orifice having second dimensions;

a second electrode disposed in a spaced-apart relationship with the first electrode, a space between the first electrode and the second electrode defining a FAIMS analyzer region;

at least a cover, comprising:

a first cover portion for covering the first ion inlet orifice when the at least a cover is in a first position and displaceable by an amount that is sufficient for uncovering a substantial area about the first ion inlet orifice when the cover is in a second position;

a second cover portion for covering the second ion inlet orifice when the at least a cover is in the second position and displaceable by an amount that is sufficient for uncovering a substantial area about the second ion inlet orifice when the cover is in the first position; and, an actuator interface for being driven by an actuator and for moving the at least a cover from the first position to the second position.

9. An apparatus according to claim 8, comprising an actuator coupled to the actuator interface, the actuator for driving the actuator interface.

10. An apparatus according to claim 9, wherein the actuator is a rotating actuator.

11. An apparatus according to claim 8, wherein the first cover portion is displaceable by an amount that is large relative to the first dimensions, and the second cover portion is displaceable by an amount that is large relative to the second dimensions.

12. A method of selecting between a first ion inlet orifice and a second ion inlet orifice of a FAIMS device, comprising:

providing a FAIMS device comprising a first electrode and a second electrode, the first electrode and the second electrode disposed in a spaced apart arrangement and defining a FAIMS analyzer region therebetween, the FAIMS device comprising a first ion inlet orifice defined within a first portion of the first electrode and a second ion inlet orifice defined within a second portion of the first electrode;

providing a rotating actuator; and, in response to rotation of the rotating actuator in a first direction, uncovering the first ion inlet orifice and covering the second ion inlet orifice, wherein the first ion inlet orifice is covered over a first range of rotational orientations of the rotating actuator and is uncovered over a second range of rotational orientations of the rotating actuator, such that accurate rotational alignment of the rotating actuator is obviated.

13. A method according to claim 12, comprising in response to rotation of the rotating actuator in a second direction opposite the first direction, covering the first ion inlet orifice and uncovering the second ion inlet orifice.

14. A method according to claim 13, wherein the second ion inlet orifice is uncovered over the first range of rotational orientations of the rotating actuator and is covered over the second range of rotational orientations of the rotating actuator.

15. A method according to claim 13, comprising translating rotational motion of the rotating actuator into a sliding motion of a cover element relative to the first electrode.

16. A method according to claim 15, wherein covering the first ion inlet orifice comprises forming a substantially gas-tight seal between the cover element and the first electrode about a periphery of the first ion inlet orifice.

17. A method according to claim 12, comprising providing a cover element, the cover element not having an opening defined therethrough that is dimensioned about the same as the first ion inlet orifice for being aligned with the first ion inlet orifice so as to uncover the first ion inlet orifice.

18. A method according to claim 12, comprising providing a cover element disposed adjacent to the first electrode and moveable between a first position in which the first ion inlet orifice is covered and a second position in which the first ion inlet orifice is uncovered.

19. A method according to claim 18, wherein movement of the rotating actuator through the second range of rotational orientations translates into movement of the cover element by an amount that is large relative to at least a dimension of the first ion inlet orifice.

* * * * *